United States Patent [19]

Evans et al.

[11] Patent Number: 4,870,009
[45] Date of Patent: Sep. 26, 1989

[54] METHOD OF OBTAINING GENE PRODUCT THROUGH THE GENERATION OF TRANSGENIC ANIMALS

[75] Inventors: Ronald M. Evans, La Jolla, Calif.; Richard D. Palmiter, Seattle, Wash.; Ralph L. Brinster, Gladwyne, Pa.

[73] Assignee: The Salk Institute for Biological Studies, San Diego, Calif.

[21] Appl. No.: 561,644

[22] Filed: Dec. 15, 1983

Related U.S. Application Data

[63] Continuation-in-part of Ser. No. 443,071, Nov. 22, 1982, abandoned.

[51] Int. Cl.$^4$ .................. C12P 21/02; C12N 15/00; C12N 5/00; C12N 1/00
[52] U.S. Cl. .................. 435/70; 435/172.3; 435/240.1; 435/320; 935/6; 935/36; 935/53; 935/63; 935/111; 800/1
[58] Field of Search .................. 435/172.3, 317, 240, 435/241, 70, 68, 240.1; 119/1; 935/6, 36, 47, 53, 63, 70, 71; 800/1

[56] References Cited

U.S. PATENT DOCUMENTS

| | | | |
|---|---|---|---|
| 4,276,282 | 6/1981 | Sugimoto et al. | 424/85 |
| 4,419,446 | 12/1983 | Howley et al. | 435/68 |
| 4,579,821 | 4/1986 | Palmiter et al. | 435/172.3 |

FOREIGN PATENT DOCUMENTS

WO82/0443 12/1982 PCT Int'l Appl. .

OTHER PUBLICATIONS

Wagner et al, PNAS USA, vol. 78, pp. 6376–6380 (Oct. 1981).
Wagner et al, PNAS USA, vol. 78, pp. 5061–5020 (Aug. 1981).
Gordon et al, PNAS USA, vol. 77, pp. 7380–7384, Dec. 1980.
Talkington et al, Promoters Structure and Function, edited by Rodriquez et al, Praeger Publishers, 307–331 (May 1981).
Palmiter et al, Nature, vol. 300, pp. 611–615, Dec. 16, 1982.
Brinster et al, Nature, vol. 296, pp. 39–42, Mar. 4, 1982.
Barta et al, PNAS USA, vol. 78, pp. 4867–4871, Aug. 1981.
Doehmer et al, PNAS USA, vol. 79, pp. 2268–2272, Apr. 1982.
Pavlakis et al, PNAS USA, vol. 78, pp. 7398–7402, Dec. 1981.
"Building Bigger Mice Through Gene Transfer", Science, vol. 218, Dec. 24, 1982, p. 1298.

Primary Examiner—Alvin E. Tanenholtz
Attorney, Agent, or Firm—Fitch, Even, Tabin & Flannery

[57] ABSTRACT

Mammalian genes that encode hormones are cloned and linked to strong promoter DNA sequences. The linked sequences are inserted in plasmids for amplification in prokaryotic cells, and multiple copies of the linked sequences are excised therefrom. Linked sequences are subsequently microinjected into fertilized eggs and the fertilized eggs are implanted into pseudo-pregnant females of the same species. As a result, transgenic animals are born having the linked sequences incorporated into their genomes and expressing the gene-encoded hormone. Because multiple copies of the linked sequences are frequently inserted and because production of the hormone is not limited to certain organs, as is the case with most endogenous hormones, the transgenic animals produce substantial amounts of the hormone. Hormone can be harvested from the living animal (and from its hormone-producing progeny) by extracting fluid, such as blood serum or ascites fluid, on a regular basis.

15 Claims, 2 Drawing Sheets

METHOD OF OBTAINING GENE PRODUCT THROUGH THE GENERATION OF TRANSGENIC ANIMALS

This application is a continuation-in-part of U.S. application Ser. No. 443,071, filed Nov. 22, 1982 in the names of R. D. Palmiter and R. L. Brinster and now abandoned.

The present invention relates generally to manipulation of genetic material for the purpose of obtaining expression product of genetic material and more particularly to the generation of transgenic animals from which gene expression product may be harvested.

BACKGROUND OF THE INVENTION

"Genetic Materials" may be broadly defined as those substances which program for and guide the manufacture of cellular (and viral) constituents and the responses of cells and viral particles to environmental changes. The genetic material of all living cells and viruses (except the so-called "RNA viruses") comprises a long chain, polymeric substance known as deoxyribonucleic acid ("DNA"). The repeating units of the DNA polymer are known as nucleotides. Each nucleotide consists of one of four nucleic acids (adenine, guanine, cytosine and thymine) bound to a sugar (deoxyribose) which has a phosphate group attached. Ribonucleic acid ("RNA") is a polymeric nucleotide comprising the nucleic acids, adenine, guanine, cytosine and uricil, bound to a ribose molecule having an attached phosphate group.

Most simply put, the programming function of genetic materials is generally effected through a process whereby DNA nucleotide sequences (genes) are "transcribed" into messenger RNA ("mRNA") polymers which, in turn, serve as templates for formation of structural, regulatory and catalytic proteins from amino acids. Protein synthesis is thus the ultimate form of "expression" of the programmed genetic message provided by the DNA sequence of a gene.

Certain DNA sequences which usually "precede" a gene in a DNA polymer provide a site for initiation of the transcription into mRNA. These are referred to as "promoter" sequences. Other DNA sequences, also usually "upstream" of a gene in a given DNA polymer, bind proteins that determine the frequency (or rate) of transcription initiation. These other sequences are referred to as "regulator" sequences. Thus, sequences which precede a selected gene (or series of genes) in a functional DNA polymer and which operate to determine whether the transcription (and eventual expression) of a gene will take place are collectively referred to as "promoter/regulator" DNA sequences.

The promoter and regulator sequences of genes are clearly susceptible to enormous structural and functional variation and, in fact, only a few such sequences in rather simple genetic systems have been thoroughly structurally and operationally characterized. Promoter/regulator sequences, in general, serve to regulate gene transcription in response to chemical (and sometimes, physical) environmental conditions in and around the cell. Many generalized "models" for the action of promoter/regulator operation in gene transcription and eventual expression in simple, prokaryotic systems have been proposed. One such model posits a "repressor" gene and a regulator sequence or "operator" sequence near the promoter of another gene. According to this model, transcription of the repressor sequence results in expression of a repressor protein which selectively binds to the operator sequence to effectively preclude gene transcription of the selected gene. An environmental "signal" (e.g., increased concentration of a chemical acted upon by the protein product of the gene in question) may operatively inactivate the repressor protein, blocking its ability to bind to the operator sequence in a way which would interrupt transcription of the gene. Increased concentrations of a substrate could be seen as operating to "induce" synthesis of the protein which catalyzes its breakdown.

Another generalized model of operation of promoter/regulator sequences in the regulation of gene transcription posits formation of an initially inactive form of repressor protein by the repressor DNA sequence. Such an inactive form could not bind to an operator DNA sequence (and disrupt selected gene transcription) until it is combined with some other substance present in the cell. The other substance could be, for example, a compound which is the product of a reaction catalyzed by the protein coded for by the selected gene. Increased concentrations of such a reaction product in the cell would thus operate to repress the potential overproduction of proteins responsible for the product's synthesis. In these examples, the regulator protein functions to inhibit transcription. Other regulatory proteins have been described which potentiate or activate transcription of specific DNA sequences. Thus, there are examples of both negative and positive control proteins and corresponding regulatory DNA sequences.

Similar "models" for the operation of promoter/regulator DNA sequences in eukaryotic cells have been proposed. See, e.g., Brown, "Gene Expression in Eukaryotes", *Science*, 211, pp. 667–674 (1981).

Among the basic problems of genetic engineering is the isolation and preparation of multiple copies of selected gene sequences of interest, together with the promoter or promoter/regulator DNA sequences which normally affect their transcription in the cells from which they are isolated. Another basic problem of genetic engineering is the insertion and stable incorporation of DNA sequences into cells in a manner which will permit external regulation of the transcription of the gene sequences and their expression.

Significant advances in the isolation and copying of selected DNA sequences have been made possible by the use of restriction endonuclease enzymes (which are capable of effecting site-specific cuts in DNA polymers) and ligating enzymes (which serve to fuse DNA sequences together). DNA sequences of interest are usually incorporated into "vectors" of plasmid or viral origin that allow selective replication in a suitable host cell (for example, bacteria, yeast, or mammalian cells). When these vectors with DNA sequences of interest are introduced into cells of higher animals or plants, they may either be maintained as extrachromosomal elements or incorporated into the chromosomes.

Most genetic engineering activity to date has been directed toward the stable incorporation of exogenous DNA in prokaryotic cells such as bacteria and in the simpler eukaryotes such as yeasts, molds and algae. The hoped-for result of these experiments has been to provide not only a source of multiple copies of selected genes, but the large scale transcription and expression of commercially significant gene in the form of proteinaceous products. See, e.g., Cohen, et al., U.S. Pat. No. 4,237,224; Manis, U.S. Pat. No. 4,273,875; and Cohen, U.S. Pat. No. 4,293,652. Work involving eukaryotic cells of higher organisms, such as plants and animals, has generally involved cells which are capable of continuous growth in culture.

It is recognized that animal cells are in several respects better hosts for recombinant animal genetic material than unicellular plants, and the more similar the animal species from which the gene is excised and the host cell is derived, the greater the likelihood that a functional product will be expressed and correctly processed. Different animal species frequently produce analogous proteins, and often considerable genetic homology is carried over from one species to another. Accordingly, an animal cell is much more likely than a bacteria or yeast cell to be able to perform the post-translational processing steps necessary for the gene-coded protein to be biologically active and much more likely to correctly translate a foreign gene having interrupted coding sequences. Techniques have been developed for introducing foreign genetic material into the genomes of animal tissue cells. These include attaching the foreign genetic material to a cloning vector, such as a modified virus or cosmid, and transfecting the cloning vector into the cell. The genetic material introduced into the cell by means of the vector will frequently incorporate into the genome.

An obstacle to using animal tissue cell cultures, particularly those obtained from higher animals, for the expression of recombinant gene product is the general inadaptability of tissue cell culture to large scale "farming". Unlike bacteria or yeast cells, which rapidly proliferate in a favorable environment, animal tissue cells are much less adaptable to mass production techniques. The cells which comprise the tissues of higher animals reproduce slowly and in many cases, having reached a mature stage, do not reproduce at all. The division of animal tissue cells is often very much influenced by the environs of other cells. Even if a tissue culture is initially provided with a generally ideal environment, the proliferation of cells changes that environment, frequently unfavorably to further proliferation. Tissue cultures are also subject to infection, and a major infection could wipe out a considerable investment of time and effort.

Because normal animal tissue cells generally have proliferation deficiencies, it is preferred to use animal cells that have been altered naturally or artificially to more freely proliferate. A number of tumor cells lines, either naturally or artificially produced, have been characterized and are available for genetic alteration. However, even with these cells, proliferation does not approach the rate achievable with bacteria or yeast cells, and their continued rapid proliferation requires that their environment be continuously monitored and adjusted.

The possibility of obtaining correctly processed animal gene products in substantially greater quantity than can be obtained in minute quantities by direct isolation from animal tissue has very important applications, particularly with respect to therapeutic applications but also with respect to agricultural needs. For example, growth hormone, a substance which is produced in the anterior lobe of the mammalian pituitary gland and regulates the growth of mammals, if produced in substantial quantities could be used therapeutically to treat genetic disorders, such as dwarfism. If produced in even greater quantities and relatively inexpensively, growth hormone could be used to increase the muscle mass or reduce the growing period of domestic animals. Other mammalian proteins whose large scale production would be of immediate benefit include human calcitonin, human growth hormone releasing factor and human blood clotting factors. Other mammalian proteins could be expected to have similar usefulness.

Of significant interest to the background of the invention are numerous publications of prior investigations relating to: (1) regulation of mammalian gene expression; and (2) introduction of purified genes into eukaryotic cells.

Specifically incorporated by reference herein for purposes of indicating the background of the invention and illustrating the state of the prior art are the following publications of co-inventor Palmiter and his co-workers: Durnam, et al., "Isolation and Characterization of the Mouse Metallothionein-I Gene", *P.N.A.S.*, 77, pp. 6511-6515 (1980); Durnam, et al., "Transcriptional Regulation of the Mouse Metallothionein-I Gene by Heavy Metals", *J. Biol. Chem.*, 256, pp. 5712-5716 (1981); Mayo, et al., "Gluocorticoid Regulation of Metallothionein-I mRNA Synthesis in Cultured Mouse Cells", *J. Biol. Chem.*, 256 2621-2624 (1981); Hager, et al., "Transcriptional Regulation of Mouse Liver Metallothionein-I Gene by Glucocorticoids", *Nature,* 291, pp. 30-342 (1981); Glanville, et al., "Structure of Mouse Metallothionein-I Gene and its mRNA", *Nature,* 292, pp. 267-269 (1981); and Beach, et al., "Amplification of the Metallothionein-I Gene in Cadmium Resistant Mouse Cells", *P.N.A.S.,* 78, pp. 2210-2214 (1981). The foregoing all deal with the DNA sequence specifying production of low molecular weight, metal-binding protein found in one or more forms in most vertebrae tissues. More particularly, the publications treat mouse metallothionein genes as well as their promoter/regulator DNA sequences and the responsiveness of the promoter/regulator sequences to metals and steroid hormones.

Additional publications of Palmiter and his co-worker which are incorporated by reference herein are: McKnight, et al., "Transferring Gene Expression, Regulation of mRNA Transcription in Chick Liver by Steroid Hormones and Iron Deficiency", *J. Biol. Chem.*, 255, pp. 148-153 (1980); and Palmiter, et al., "Steriod Hormone Regulation of Ovalbumin and Conalbumin Gene Transcription, A Model Based Upon Multiple Regulatory Sites and Intermediary Proteins", *J. Biol. Chem.*, 256, pp. 7910-7916 (1981).

Also incorporated by reference herein is a publication of Brinster and his co-workers dealing with microinjection of plasmids into germinal vesicles of mouse oocytes or pronuclei of fertilizes mouse ova, Brinster, et al., "Mouse Oocytes Transcribe Injected Xenopus 5S RNA Gene", *Science,* 211, pp. 396-398 (1981).

Also incorporated by reference herein are publications of Evans and co-workers dealing with hormone releasing factor mRNA sequences and also dealing with the cloning of rat growth hormone genes and their introduction into and expression in mammalian cells: Harpold, M. M., P. R. Dobner, R. M. Evans and F. C. Bancroft. Construction and identification by positive hybridization-translation of a bacterial plasmid containing a rat growth hormone structural gene sequence. *Nucleic Acids Research* 5, 2039-2053 (1978); Harpold, M. M., P. R. Dobner, R. M. Evans, F. C. Bancroft and J. E. Darnell, Jr. The synthesis and processing of a nuclear RNA precursor to a rat pregrowth hormone messenger RNA. *Nucleic Acids Research* 6, 3133-3144

(1979); Soreq, H., M. Harpold, R. M. Evans, J. E. Darnell, Jr. and F. C. Bancroft. Rat growth hormone gene: Intervening sequences separate the mRNA regions. *Nucleic Acids Research* 6, 2471–2482 (1979); Doehmer, J., Barinaga, M., Vale, W., Rosenfeld, M. G., Verma, I. M. and Evans, R. M. Introduction of rat growth hormone gene into mouse fibroblasts via a retroviral DNA vector: Expression and regulation. *Proc. Natl. Acad. Sci. U.S.A.* 79, 2268–2272 (1982); Evans, R. M., Birnberg, N. C. and Rosenfeld, M. G. Glucocorticoid and thyroid hormone transcriptionally regulate growth hormone gene expression. *Proc. Natl. Acad. Sci. USA,* 79, 7659–7663 (1982); Mayo, K. E., Vale, W., Rivier, J., Rosenfeld, M. G. and Evans, R. M. Expression cloning and sequence of a cDNA encoding human growth hormone releasing factor. *Nature,* In Press (1983); Barinaga, M., Yamomoto, G., Rivier, C., Vale, W., and Evans, R. M. Growth hormone releasing factor transcriptionally regulates growth hormone expression. *Nature,* In press (1983); Verma, I., Doehmer, J., Barinaga, M., Vale, W., Rosenfeld, M. and Evans, R. M. In: *Eukaryotic Viral Vectors,* Expression and Regulation of Rat Growth Hormone Gene in Mouse Fibroblasts (1982); and Palmiter, R. D., Brinster, R. L., Hammer, R., Trumbauer, M., Rosenfeld, M. G., Birnberg, N. C. and Evans, R. M. Dramatic growth of mice that develop from eggs microinjected with metallothionein-growth hormone fusion genes. *Nature,* 300, 611–615 (1982).

Also pertinent to the background of the present invention and incorporated by reference herein, are the publications of Illmensee, et al., *Cell,* 23, pp. 9–18 (1981) and Gordon, et al., *P.N.A.S.,* 77, pp. 7380–7384 (1981) which respectively treat injection of nuclei into enucleated mouse eggs and introduction of plasmids containing the herpes thymidine kinase gene and SV40 (Simian viruses) in mice. Finally, the recent publication of Wagner, et al. appearing in *P.N.A.S.,* 78, pp. 5016–5020 (1981) and treating incorporation of the human B-globin gene and a functional viral thymidine kinase gene into developing mice, is pertinent to the background of the present invention.

SUMMARY OF THE INVENTION

The present invention provides novel methods and materials for obtaining valuable mammalian hormones which are the expression of external genes introduced into the genetic material of animals. A mammalian chromosome segment, including a gene that encodes the desired hormone product, is isolated, and an appropriate promoter chromosomal sequence is in linked thereto. It is advantageous that the linked promoter sequence be a strong promoter. Retroviral gene promoters also provide strong promotion and may be linked to mammalian gene in accordance with the invention. A fertilized mammalian egg is obtained and the linked chromosome fragments are introduced, e.g., by microinjection, into the egg. Then, the fertilized egg having the linked chromosome fragments is implanted into a host female animal of the species from which the fertilized egg was obtained so that the host female animal gives birth to a transgenic animal that develops from its fertilized egg. The transgenic animal produces the hormone in amounts very substantially greater than it produces analagous endogenous protein, and the hormone is harvested from the transgenic animal, e.g., from its serum or ascites fluid. The living transgenic animal and its hormone-producing progeny (which for purposes of this invention are considered the equivalent of the first generation transgenic mammal) is a continuous source of the gene-encoded hormone.

In one aspect of the invention control of transcription of any selected chromosomal or extrachromosomal gene or DNA sequence is provided through the selection of a promoter/regulator DNA sequence which is functionally responsive to environmental variations in the concentration of metals and/or steriod hormone compounds.

Promoter/regulator DNA sequences suitable for use in practice of the invention are derived from avian and mammalian cells and include: the iron and steroid hormone-responsive promoter/regulator sequence naturally associated with the transferring (conalbumin) gene of chickens; the steroid hormone-responsive promoter/regulator sequence associated with ovalbumin gene in chickens; and the metal and steroid hormone-responsive promoter/regulator sequence of the mouse metallothionein-I or metallothionein II genes.

The invention, however, is not limited to promoters with associated regulator DNA sequences. Examples of promoter DNA sequences which are not either metal or steriod- or hormone-responsive which might be employed include: liver promoters, i.e. albumin, glycolytic enzymes, transferring, caeruloplasmin and alpha-2-microglobulin, histocompatibility gene promoters, immunoglobulin gene promoters, interferon gene promoters, heat shock gene promoters and retroviral gene promoters.

Novel fusion gene products of the invention include selected DNA sequences to which are ligated promoter DNA sequences including promoter/regulator DNA sequences, as described above. These products may be incorporated into DNA plasmid and viral vectors to provide useful tools in the transformation of the fertilized eggs of a wide variety of mammalian animals.

Other aspects and advantages of the present invention will be apparent upon consideration of the following detailed description thereof and the drawing wherein.

DETAILED DESCRIPTION

The following illustrative examples are directed to: (a) preparation of fusion genes, e.g., as illustrated by plasmid pMGH; (b) injection of plasmids into fertilized, one-cell mammalian eggs, e.g., mouse eggs, and the manipulation of injected eggs permitting growth of adult animals, e.g., mice, therefrom; (c) determination of the extent of stable incorporation, transcription and expression of exogenous (e.g., viral thymidine kinase) genes in the adult animals; (d) mammalian cell culture transformations using, plasmids, e.g., the pMGH plasmid, and effects of metals on exogenous gene expression in the transformed cells; (e) studies of the transcription and expression of an exogenous gene in mammalian embryos injected with the plasmid; (f) preparation of fusion genes, e.g., as illustrated by plasmid pMGH; (g) injection of plasmid, e.g., pMGH plasmid, into fertilized, one-cell mammalian, e.g., mouse, eggs and the manipulation of injected eggs permitting growth of adult mammals therefrom; (h) determination of the extent of stable incorporation, transcription and expression of an exogenous (e.g., growth hormone) gene in the adult animal; and (i) harvesting of the expression products of the exogenous gene from the transgenic animal.

EXAMPLE I

This example relates to procedures for preparation of a fusion gene of the present invention. In this example, a DNA plasmid, pMGH, is shown to include a DNA sequence coding for a rat growth hormone (GH) structural gene which is operatively associated with the promoter/regulator DNA sequence of the mouse metallothionein-I (MT-I) gene. The MT portion of the fusion gene was constructed using plasmid $m_1pEE_{3.8}$, a plasmid in which the 3.8 kb EcoRI-EcoRI fragment of me-lambda26 is inserted at the EcoRI site of pBR322, disclosed in Durnam, et al., *P.N.A.S.*, 77, pp. 6511–6515 (1980). The GH portion was constructed using plasmid pGGB disclosed in Doehmer et al. *P.N.A.S.*, 79, pp. 2268–2272 (1982).

Figure 1A:
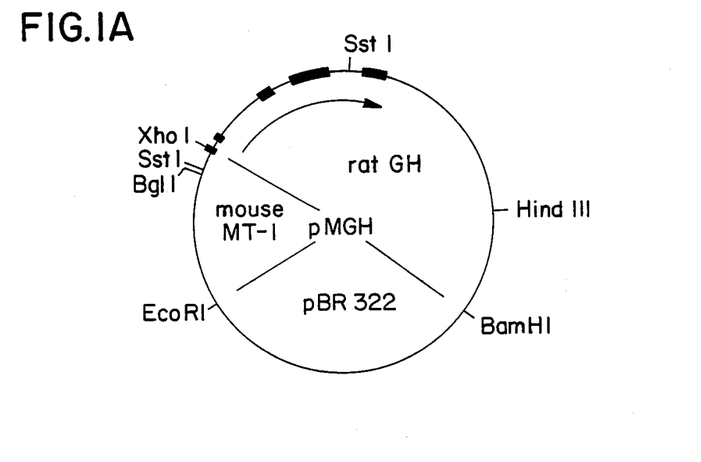
FIG. 1 depicts construction of DNA plasmid pMGH which incorporates a fusion gene product of the invention and FIG. 2 graphically represents growth characteristics of mice developed from eggs microinjected with fusion gene products of the invention.
Figure 1B:
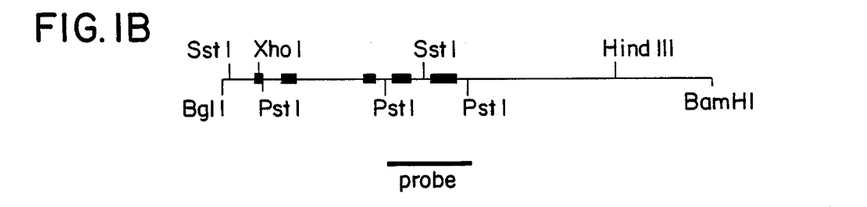
Figure 1C:
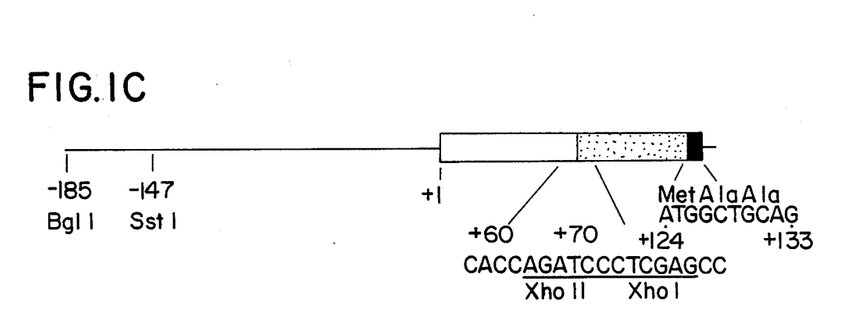

As illustrated in FIG. 1, part A, a fragment of the cloned genomic rat growth hormone gene, from which the 5' regulatory region had been deleted, was fused at the Salk Institute to a MT-I promoter/regulator region to form plasmid pMGH. More specifically, the unique Bgl II site of the MT-I genomic clone $m_1pEE_{3.8}$ was converted to an Xho I site by digesting with Bgl II, followed by filling in the sticky ends with Klenow fragment of DNA polymerase in the presence of ATP, GTP, CTP and TTP. Xho I linkers (5'-CCTCGAGG-3') were then ligated to the blunt ends and *E. coli* bacterial strain $RR_1$ was transformed with this DNA. The Pvu II site of pBR322 was converted to a Bam HI fragment containing the MT-I promoter and pBR 322 DNA was ligated to a 4.8 kb Xho I - Bam HI fragment containing the rat GH structural gene [See Doehmer, et al., *P.N.A.S.*, 79, pp. 2268–2272 (1982)] to give pMGH (8.9 kb). FIG. 1, Part B illustrates the fragment used for subsequent injection studies, i.e., a 5.0 kb Bgl I - Bam HI fragment which was isolated from an agarose gel by the $NaClO_4$ method of Chen, et al., *Anal. Biochem.*, 101, pp 339–341 (1980). For genomic Southern blots, a 1.0 kb Pst I fragment spanning exons 4 and 5 was isolated and nick-translated [see, Palmiter, et al., *Cell*, 29, pp. 701–710 (1982)] and then used as a hybridization probe. In FIG. 1, Part C the predicted structure of exon 1 of the fusion gene is shown. The line and open box represent MT-I untranslated sequences, the stippled box represents GH untranslated sequences and the solid box represents the beginning of the GH coding region.

The fusion gene is predicted to direct transcription of an mRNA containing 68 bases contributed by MT-I, followed by 1 base contributed by an Xho I linker, followed by the rat GH mRNA sequence starting at nucleotide 7. This construction preserves the (mRNA) AUG initiation codon for GH synthesis located at position 124–126 (FIG. 1, Part C), the four intervening sequences and the poly(A) site of the rat GH gene (FIG. 1, Part B) and 3 kb of downstream chromosomal sequences.

EXAMPLE II

This example relates to use of a fragment of the fusion gene-carrying plasmid, pMGH, as a vector for microinjection studies similar to those of prior Example I. A 5.0 kb fragment extending from the Bgl I site of MT-I (-185) to Bam HI (see FIG. 1, Part B) was restricted from pMGH, separated from other fragments on an agarose gel and used for injection into eggs. This linear fragment with heterologous ends was chosen because experience has suggested that such fragments integrate into host DNA more efficiently than supercoiled plasmids. The male pronuclei of fertilized eggs were microinjected with 2 picoliters containing about 600 copies of this fragment, and 170 eggs were inserted into the reproductive tracts of foster mothers as in Example I. Twenty-one animals developed from these eggs.

EXAMPLE III

This example relates to assays performed on tissue of mice developed according to Example II. When the mice were weaned, total nucleic acids were extracted from a piece of tail and used for DNA dot hybridization to determine which animals carried MGH sequences. Using the Pst I probe of FIG. 1, Part B, seven of the animals (designated MGH 2, 3, 10, 14, 16, 19 and 21) gave hybridization signals above background and their DNA was analyzed further by restriction with Sst I and Southern blotting. This analysis showed that all seven had an intact 1.7 kb Sst I fragment predicted from the restriction map shown in FIG. 1. All of the animals with a prominent 1.7 kb hybridizing band also revealed a 3.3 kb band. This band is predicted from a circularized version of the 5.0 kb Bgl I - Bam HI fragment. Two of the mice with multiple copies (MGH-10 and 19) gave a 5.0 kb hybridizing fragment when digested with Hind III, an enzyme that cuts only once within the injected fragment. Suprisingly, Bam HI also generates a 5.0 kb hybridizing fragment in all of the DNAs analyzed (MGH-10, 14, 16 and 19), suggesting that this restriction site was restored during circularization, whereas Bgl I and Eco RI (which does not cut within the fragment) gave larger fragments. From the above, it can be concluded that all of the MGH positive animals have at least one intact Bgl I - Bam HI insert and four of the mice have a tandem head-to-tail duplication of this 5.0 kb fragment; however, the details of how and when this fragment circularized and integrated are impossible to discern.

At 33 days post parturition, all of the mice were weaned and maintained on a solid diet supplemented with water containing 5000 ppm $ZnSO_4$ (76 mM) and their growth rate was recorded periodically. The dose of Zn was chosen on the basis of experiments indicating that 5000 ppm induced nearly maximal levels of MT-I mRNA in the liver without impairing the breeding potential of mice maintained on this diet for many months.

Figure 2:
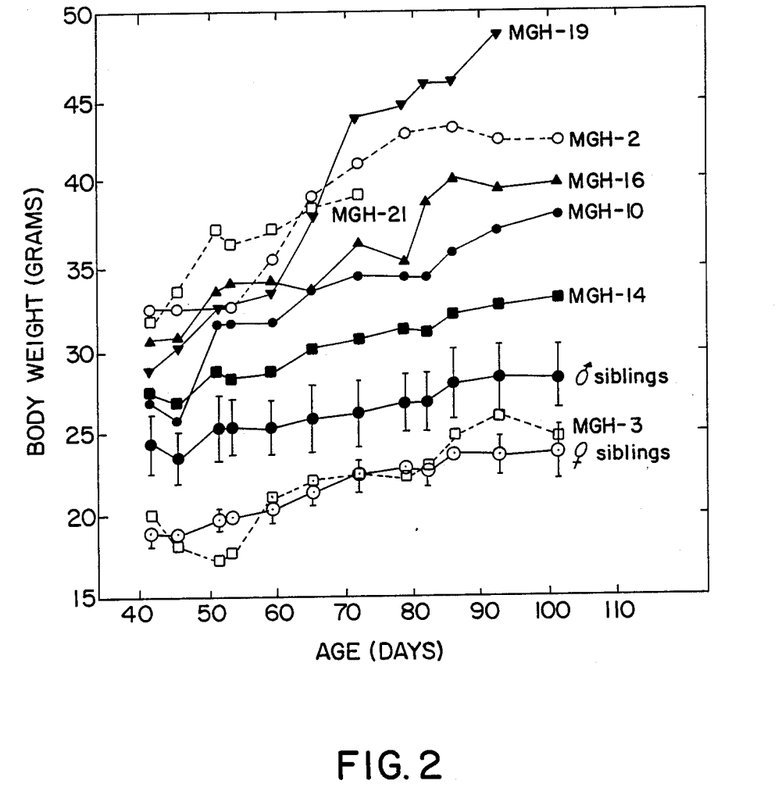

FIG. 2 shows the growth of the seven mice that contain MGH sequences. The litter mates without MGH sequences serve as convenient controls; the weights for each sex are averaged separately. The body weights of the males are shown in solid symbols; the mean weight $\pm$S.D. of 11 siblings not containing MGH sequences is also shown. The female weights are shown in open symbols; mean $\pm$S.D. of 3 siblings are indicated. MGH-21 died on day 72.

Six of the mice with MGH sequences showed substantially more weight gain (up to 1.8-fold) than the controls. With the exception of MGH-16, there is a correlation between weight gain and MGH gene dosage. The animal with the most copies of MGH sequences, MGH-21, died after 7 weeks of rapid growth; other mice have, however, grown larger.

Based upon earlier studies with mice, maximal expression of MGH was predicated in liver, intestine and kidney. Evaluation of the tissue specificity of MGH gene expression was initiated by analysis of its activity in liver. A partial hepatectomy on day 56 permitted isolation of and quantitation of RNA for MGH specific sequences by RNA slot hybridization. The level of MGH mRNA expression in the liver correlated with the growth of the transgenic mice. The largest animals MGH-2, 19 and 21 contained high amounts of MGH mRNA in the liver, whereas MGH-10, 14 and 16 with a lower growth rate contained levels of MGH mRNA that are about 50-fold lower. Analysis of samples exposed to base hydrolysis prior to spotting the nucleic acids onto nitrocellulose or treatment with RNases A plus $T_1$ after hybridization established that RNA rather than potentially contaminating DNA is hybridizing to the probe. From these data, it was estimated that 30 μg of liver RNA from MGH-2, 19 and 21 contained the same amount of GH mRNA as 13, 25 and 50 ng of poly(A) rat pituitar RNA, respectively. The RNA standard used contains about 10% GH mRNA on the basis of Rot analysis and it was therefore estimated that there are approximately 800 to 3000 MGH mRNA molecules per liver cell in these transgenic mice.

If all processing signals in the fusion gene are correctly being recognized, a fusion mRNA (63 nucleotides larger than bona fide rat GH mRNA) would be generated. Denaturing gel eletrophoresis and RNA Northern blot analysis of the liver RNA from MGH-21 showed that its size is indistinguishable from authentic mouse and rat pituitary GH mRNA. Liver RNA from a control mouse shows no GH-reactive sequences. Because the GH DNA probe used for the RNA blot analysis recognizes both rat and mouse GH mRNAs, it was necessary to establish that the hybridizing species in the liver is actually the product of the fusion gene and not mouse GH mRNA due to an unexpected activation of the endogenous mouse GH gene. The use of an Xho I linker for the construction of the fusion gene generates a sequence that will be uniquely present in MGH mRNA. Thus, the Xho I site of pMGH was labeled using $Y^{32}P$-ATP and polynucleotide kinase followed by cleavage with Sst I. This 217 nucleotide fragment was gel purified, denatured, and used as hybridization probe in a single-strand specific nuclease protection assay. Hybridization to MGH mRNA should generate a 74 base nuclease-resistant fragment while mouse GH mRNA or metallothionein mRNA will be unable to protect the kinased end and should therefore be negative. The results of this analysis showed that the predicted 74 base fragment is present in liver RNA of mouse MGH-21, but not in normal mouse pituitary RNA, control mouse liver RNA or in the liver RNA of MGH-3, an animal negative for growth. Thus, it appears that transcription is initiating properly at the MT-I promoter and continuing through the putative termination site of the GH gene, that the four GH intervening sequences are being properly spliced and that the MGH mRNA is polyadenylated.

The correlation between MGH mRNA levels and growth of the mice suggests that expression of the MGH gene accounts for the observed biological consequences. This prediction was supported by the three independent RNA analyses above, and together predict the circulating levels of GH should be elevated. Blood was drawn from the transgenic mice as well as from litter mates and assayed for GH by radioimmunoassay (RIA) according to the procedures of Doehmer, et al., *P.N.A.S.*, 79, pp. 2268–2272 (1982). The results are set out in cumulative Table 1, below.

TABLE 1

| Mouse | Sex | MGH genes (a) number/cell | MGH mRNA(b) molecules/cell | Growth Hormone(c) μg/ml | Growth grams | ratio |
|---|---|---|---|---|---|---|
| MGH-2 | O | 20 | 800 | 57 | 41.2 | 1.87 |
| MGH-3 | O | 1 | 50 | 0.87 | 22.5 | 1.02 |
| MGH-10 | O | 8 | 50 | 0.28 | 34.4 | 1.32 |
| MGH-14 | O | 2 | 50 | 0.31 | 30.6 | 1.17 |
| MGH-16 | O | 2 | 50 | 17.9 | 36.4 | 1.40 |
| MGH-19 | O | 10 | 1500 | 32.0 | 44.0 | 1.69 |
| MGH-21 | O | 35 | 3000 | 112.0 | 39.3 | 1.78 |
| female littermates (n = 3) | | 0 | 0 | 0.16 ± .1 | 22.0 ± 0.8 | |
| male littermates (n = 11) | | 0 | 0 | 0.15 ± .08 | 26.0 ± 2 | |

(a) Estimated by DNA dot hybridization and scintillation counting.
(b) Estimated from RNA slot hybridization.
(c) Measured by radioimmunoassay (RIA) as described by Doehmer, et al.
(d) Animal weights when 64 days old. The ratio of body weight compared to littermates of same sex is indicated (See also. FIG. 3)

The values for four of the transgenic mice are 100 to 800 times greater than levels in control litter mates; one mouse had 112 μg/ml of GH in its serum. Two of the transgenic mice with slower but significantly elevated growth rate had serum levels of GH that fell at the high end of the normal range. The lack of physiological regulation and the ectopic production of GH in these animals probably account for their accelerated growth. The precise effect of Zn on the growth rate has not yet been completely evaluated. It is clear, as shown in FIG. 2, that most of the animals were already larger than normal before the Zn diet was instituted. Furthermore, one of the animals (MGH-19) was removed from the Zn diet on day 56 and it continued to grow at an accelerated rate. It is possible that mice with many copies of the MGH gene produce excess GH constitutively without a requirement for heavy metal induction. Thus, the question of Zn-dependent growth will be most easily answered with analysis of offspring of mice. It may preliminarily be noted that one of the mice, MGH-10, has transmitted the MGH genes to half (10 of 19) of its offspring, suggesting that these genes are stably integrated into one of its chromosomes. The ten offspring carrying the MGH gene were divided into two groups of 5 mice. After Weaning, one group had its diet supplemented with 5000 ppm $ZnSO_4$, while the other did not. Those to whom zinc was administered displayed circulating GH levels (as measured by RIA) approximately 10-fold in excess of the "controls".

These data strongly suggest that the altered phenotype of these mice is a direct result of the integration and expression of the metallothionein-growth hormone fusion gene. The extraordinary level of GH present in some of these mice corresponds to a high level of MGH mRNA in the liver (up to 3000 molecules/cell). The amount of MGH mRNA accumulation in the liver is comparable to the endogenous level of MT-I mRNA, but about 100 fold higher than that obtained from metallothionein-thymidine kinase fusion genes studied previously. This difference is likely to be the consequence of the intrinsic stability of the GH mRNA relative to TK mRNA; however, differences in transcription rates of processing efficiency due to variations in fusion gene construction are also possible. The high level of MGH gene expression in transgenic mice will greatly facilitate direct comparison of MGH and MT-I mRNA production in different tissues, thus allowing access to the question of whether chromosomal location has an important influence on tissue specific expression of the MT-I promoter.

Growth hormone levels in some of the transgenic mice were up to 800 fold higher than in normal mice, resulting in animals nearly twice the weight of their unaffected litter mates. This superphysiological accumulation of GH undoubtedly reflects both the lack of normal feedback mechanisms and expression of this gene in many large organs including liver, kidney and intestine. The effect of chronic exposure to high levels of GH is well-documented [see, Richmond, et al., *J. Neurosurg.*, 49, pp 163-167 (1978),]resulting in the clinical condition referred to as gigantism. This condition in humans is usually associated with pituitary adenomas and more rarely with ectopic expression of GH by lung carcinomas.

Some of the diverse effects of GH are mediated directly by the hormone. However, it is generally believed that the major effect of GH is stimulation of somatomedin production in the liver. Somatomedins are insulin-like growth factors that promote proliferation of mesodermal tissues such as muscle, cartilage and bone. The involvement of somatomedins in GH response provides an explanation for the growth of animals such as MGH-10, 14 and 16 in which the circulating level of GH was only slightly higher than normal. In these animals, GH produced in the liver may be sufficient to stimulate somatomedin production because the local GH concentration is relatively high. Thus, in these animals GH may mimic the local paracrine function of some hormones.

As previously noted, other promoter sequences, including metal and/or steroid hormone-responsive promoter/regulator sequences, suitable for use in practice of the invention are useful. Preferably, these would include those of mammalian and avian cell origin. Promoter/regulator sequences may be responsive to a variety of steroids including estrogens, progestins and androgens as well as glucocorticoids.

EXAMPLE IV

This example relates to procedures for preparation of another fusion gene of the present invention. In this example, a DNA plasmid, pMThGH, is shown to include a DNA sequence coding for human growth hormone structural gene which is operatively associated with the promoter/regulator DNA sequence of the mouse metallothionein-I (MT-I) gene. Mouse metallothionein sequences were obtained from plasmids described in example I.

A fragment of a clone genomic human growth hormone (hGH) gene, from which the 5' regulatory region has been deleted, is fused to a MT-I promoter/regulator region to form plasmid pMThGH. More specifically, a Bam HI linker sequences was inserted between the +6 position of mouse MT-I gene and the Pvu II site of pBR322. Then a 2.15-kb Bam HI fragment, including the hGH structural gene, was excised from a hGH genomic clone and inserted into the Bam HI site of the MT-1 vector to give a 6.3 kb plasmid. The fusion gene is predicted to direct transcription of an mRNA containing 6 bases contributed by MT-I, followed by 2 bases contributed by a Bam HI linker, followed by the entire human growth hormone sequence.

A fragment of the fusion gene extending from the Bst EII site of MT-I and including the Bam HI fragment is restricted from pMThGH and separated from other fragments on an agarose gel and used for injection into eggs. The male pronuclei of fertilized eggs are microinjected with 2 picoliters containing about 1,000 copies of this fragments, and the fertilized eggs are inserted into the reproductive tracts of foster mothers. 101 mice develop from these eggs.

When the mice are weaned, total nucleic acid is extracted from a piece of tail and used for DNA dot hybridization to determine which animals carry MThGH sequences. Using a nick-translated probe complementary to the hGH gene, 33 of the animals give hybridization signals above background.

7 to 21 weeks post parturition, peripheral blood serum is obtained from each of the hybridization probe-positive mice. The presence of human growth hormone in the sera is determined by radioimmunoassay using antibody raised against human growth hormone. The level of human growth hormone in the mice sera is determined by radioimmunoassay to range from about 0 to about 143,000 nanograms per milliliter. It compares with the levels of mouse growth hormone normally present in mouse sera (100 nanograms per ml) and with the level of human growth hormone normally present in human peripheral blood at a level of 143,000 nanograms per ml.

The fluid is frozen until 10 ml of fluid is collected, whereupon the fluid is pooled. Human GH is purified from the pooled fluid according to standard protein purification protocols. 1.43 mg of substantially purified human growth hormone is obtained. This corresponds to multiple daily dosages of human GH for the treatment of human dwarfism. This example demonstrates that valuable mammalian hormones are obtainable from transgenic animals produced in accordance with the present invention.

EXAMPLE V

This example relates to procedures for preparation of another fusion gene of the present invention. In this example, a DNA plasmid, pMThGRF, is shown to include a DNA sequence coding for human growth hormone releasing factor (hGRF) structural gene which is operatively associated with the promoter/regulator DNA sequence of the mouse metallothionein-I (MT-I) gene. The Metallothionein portion of the fusion gene is prepared as described in Example 1.

A fragment of a cloned human growth hormone releasing factor gene, from which the 5' regulatory region has been deleted, is fused to a MT-I promoter/regulator region to form plasmid pMhGRF. More specifically, the unique Bgl II site of the MT-I genomic clone m₁pEE₃.₈ is destroyed by digesting with Bgl II, followed by filling in the sticky ends with Klenow fragment of DNA polymerase in the presence of ATP, GTP, CTP and TTP. This plasmid is digested with Pvu II and is ligated to the blunt ends of a Sma I to Sma I fragment containing the human GRF structural gene to give MThGRF (8.3 kb). A 4.3 KB Bst EII to Sma I fragment is used for subsequent injection studies. The fusion gene is predicted to direct transcription of an mRNA containing 68 bases contributed by MT-I, followed by the entire human GRF sequence.

The 4.3 kb fragment fusion gene extending from the Bst EII site of MT-1 to the Sma I site of GRF is restricted from MThGRF and separated from other fragments on an agarose gel and used for injection into eggs. The male pronuclei of fertilized eggs are microinjected with 2 picoliters containing about 1,000 copies of this fragment, and 170 eggs are inserted into the reproductive tracts of foster mothers. 20 mice develop from these eggs.

When the mice are weaned, total nucleic acid is extracted from a piece of tail and used for DNA dot hybridization to determine which animals carry MThGRF sequences. Using a nick-translated probe complementary to the hGRF gene, 7 of the animals give hydridization signals above background, and their DNA is analyzed further by restriction enzyme digestion and Southern blotting. This analysis showed that all 7 animals have predicted intact hGRF fragment. 7-21 weeks post parturition, peripheral blood serum is obtained from each of the hybridization probe-positive mice. The presence of human growth hormone releasing factor in the sera is determined by radioimmunoassay using antibody raised against human GRF according to the method of Vale et al. The level of human GRF in the mice sera is determined by radioimmunoassay to range from about 0 to about 1,000 ng per milliliter. GRF is normally not present in the peripheral blood of either mice or humans in amounts approaching nanogram per ml concentrations.

Sera is withdrawn weekly from one mouse, producing human GRF in its peripheral blood at a level of 1,000 ng per ml. The fluid is frozen until 10 ml of fluid is collected, whereupon the fluid is pooled. Human GRF is purified from the pooled fluid according to the method of Vale et al. 1 mg of substantially purified human GRF is obtained. This example further demonstrates that valuable mammalian hormones are obtainable from transgenic animals produced in accordance with the present invention.

EXAMPLE VI

This example relates to procedures for preparation of another fusion gene of the present invention. In this example, a DNA plasmid, pThGRF, is shown to include a DNA sequence coding for human growth hormone releasing factor structural gene which is operatively associated with the promoter/regulator DNA sequence of the chicken transferring gene. The fusion gene is constructed using plasmid p17 disclosed in McKnight, et al., *Cell*, 34, p. 335-341 (1983).

A fragment of a cloned GRF from which the 5' regulatory region has been deleted is fused to a transferring promoter/regulator region to form plasmid pThGRF. More specifically, the unique EcoRI site in the first intervening sequence of the transferring genomic clone p17 is destroyed by digesting with EcoRI, followed by filling in the sticky ends with Klenow fragment of DNA polymerase in the presence of ATP, GTP, CTP and TTP. This plasmid is digested with Pvu II and is ligated to the blunt ends of a Sma I to Sma I fragment containing the entire human growth hormone releasing factor structural gene to give pThGRF. A 7.3 Kb to Sma I fragment is used for subsequent injection studies which is isolated from an agarose gel by the NaClO₄ method of Chen, et al., *Anal. Biochem.*, 101, pp. 339-341 (1980). The fusion gene is predicted to direct transcription of an mRNA containing 5' untranslated sequences contributed by the transferring gene, followed by the entire GRF gene.

The 7.3 kb fragment fusion gene extending from the KpnI site of transferring (-185) to the Sma I site of GRF restricted from ThGRF and separated from other fragments on an agarose gel and used for injection into eggs. The male pronuclei of fertilized eggs are microinjected with 2 picoliters containing about 1,000 copies of this fragment, and 170 eggs are inserted into the reproductive tracts of foster mothers as in Example I and V. 20 mice develop from these eggs.

When the mice are weaned, total nucleic acid is extracted from a piece of tail and used for DNA dot hybridization to determine which animals carry pThGRF sequences. Using a nick translated probe complementary to the GRF gene, 7 of the animals give hybridization signals above background and their DNA is analyzed further by restriction with restriction enzymes and Southern blotting. This analysis shows that all 7 have a predicted intact hGRF fragment. 7-21 weeks post parturition, peripheral blood serum is obtained from each of the hybridization probe-positive mice. The presence of human growth hormone releasing factor in the sera is determined by radioimmunoassay according to the method of Doehmer, J. et al. *Proc. Nat'l. Acad. Sci. U.S.A.* 79, 2268 (1982), using antibody raised against GRF as described in Rivier et al., *Nature* 300, p. 276 (1982). The level of GRF in the mice sera is determined by radioimmunoassay to range from about 0 to about 1,000 ngm per milliliter.

Sera is withdrawn daily form one mouse that is producing GRF in its peripheral blood at a level of 1,000 ngm per ml. The fluid is frozen until 10 ml of fluid is collected, whereupon the fluid is pooled. hGRF is purified from the pooled fluid according to the method of Rivier et al., *Nature* 300, p. 276 (1982). 1 mgm of substantially purified GRF is obtained. This example further demonstrates that valuable mammalian hormones are obtainable from transgenic animals produced in accordance with the present invention.

While plasmid vectors, as exemplified by pMGH, pMThGH and pMThGRF and pThGRF are suitable for many embryo injection and transformation procedures according to the invention, it will be understood that many other vectors can be constructed to carry a DNA sequence of choice to which is fused a promoter/regulator DNA sequence.

The above examples demonstrate the feasibility of "gene farming", i.e., producing a transgenic animal and raising or farming the animal for the purpose of obtaining the product of its expressed gene. The success with producing transgenic animals which produce very elevated amounts of the product of the introduced gene is illustrative of the value of this method for obtaining unprecedented quantities of gene product. For example, the concentrations of GH in MGH-21 serum was 10–100 fold higher than that reportedly harvested from bacterial or mammalian cell cultures that were genetically engineered for GH production [see, Goedell, et al., *Nature*, 281, pp. 544–548 (1979), Pavlakis, et al., *P.N.A.S.*, 78, pp. 7398–7402 (1981); Doehmer, et al., *P.N.A.S.*, 79, pp. 2268–2272 (1982); and Robins, et al., *Cell*, 29, pp. 623–631 (1982)]. This "genetic farming" concept is comparable to the practice of raising valuable antisera in animals except that a single injection of a gene into a fertilized egg substitutes for multiple somatic injections; moreover, the expression of the selected gene is quite likely to be heritable. This approach is particularly applicable in those cases where the protein of interest requires special covalent modifications (e.g., proteolytic cleavage, glycosylation, or y-carboxylation) for activity or stability.

Consequently, only such limitations as are set out in the claims should be placed thereon.

What is claimed is:

1. A method of producing a mammalian hormone, which method comprises
    providing a linerized DNA chain including a promoter/regulator sequences from a mammalian metallothionein gene and a linked sequence that encodes said mammalian hormone under the promotional control of said promoter/regulator sequence,
    obtaining fertilized mammalian eggs,
    introducing said linearized DNA chain by microinjection into the male pronuclei of said fertilized mammalian eggs to genetically alter the same,
    implanting said altered fertilized eggs into host female animals of the species from which said fertilized mammalian eggs were obtained so that the host female animals give birth to animals that develop from said implanted, altered eggs,
    selecting those of said developed animals which produce said mammalian hormone in amounts very substantially greater than normal,
    harvesting peripheral blood sera from said selected animals, and
    isolating said very substantially greater than normal amounts of said hormone from said harvested sera.

2. A method according to claim 1 wherein said DNA chain is provided by isolating said promoter/regulator sequence, independently isolating said sequence that encodes a mammalian hormone and linking said sequences.

3. A method according to claim 1 wherein said second sequence encodes growth hormone.

4. A method in accordance with claim 3 wherein said second sequence encodes rat growth hormone.

5. A method according to claim 3 wherein said second sequence encodes human growth hormone.

6. A method according to claim 1 wherein a said transgenic animals that develop from said fertilized eggs produce an endogenous hormone identical to or analogous to said linked sequence-encoded hormone, said transgenic animal being selected producing said linked sequence-encoded hormone at levels of between about 10 and about 1000 times the level at which it produces the corresponding endogenous hormone.

7. A method according to claim 1 selecting animals having chromosomes incorporating multiple copies of said DNA chain.

8. A method according to claim 7 selecting animals that have chromosomes incorporating at least about 5 copies of said DNA chain.

9. A method of producing a mammalian hormone, which method comprises
    proving a linearized DNA chain including a first sequence which is the promoter/regulator sequence from a mammalian metallothionein gene and a second sequence operably linked to said first sequence that encodes a mammalian hormone,
    obtaining a fertilized mammalian egg,
    introducing said linearized DNA chain by microinjection into the male pronuclei of said fertilized mammalian egg to genetically alter the same,
    implanting said altered fertilized egg into a host female animal of the species from which said fertilized mammalian egg was obtained so that said host female animal gives birth to a transgenic animal that develops from said implanted egg and which produces said hormone in amounts at least 10 times greater than the level at which it produces the corresponding endogenous hormone,
    harvesting peripheral blood sera from said transgenic animal, and
    isolating said mammalian hormone from said harvested sera.

10. A method according to claim 9 wherein said promoter/regulator sequence is form a mouse gene.

11. A method in accordance with claim 9 wherein said promoter/regulator sequence is from a mouse MT-1 gene.

12. A method according to claim 11 wherein said hormone-encoding sequence encodes rat growth hormone.

13. A method according to claim 11 wherein said hormone-encoding sequence encodes human growth hormone.

14. A method according to claim 1 wherein said promoter/regulator sequence is from a mouse gene.

15. A method in accordance with claim 13 wherein said promoter/ regulator sequence is from a mouse MT-1 gene.

* * * * *

UNITED STATES PATENT AND TRADEMARK OFFICE
CERTIFICATE OF CORRECTION

PATENT NO. : 4,870,009
DATED : September 26, 1989
INVENTOR(S) : Ronald M. Evans It is certified that error appears in the above-identified patent and that said Letters Patent is hereby corrected as shown below:

Column 15, Line 22:    Change "linerized" to --linearized--.

Column 15, Line 23:    Change "sequences" to --sequence--.

Column 16, Line 1:     After "wherein" delete "a".

Column 16, Line 39:    Change "form" to --from--.

Column 16, Line 51:    Change "13" to --3--.

Signed and Sealed this

Thirtieth Day of April, 1991

*Attest:*

HARRY F. MANBECK, JR.

*Attesting Officer*     *Commissioner of Patents and Trademarks*